US008283327B2

(12) United States Patent
Kneller

(10) Patent No.: US 8,283,327 B2
(45) Date of Patent: *Oct. 9, 2012

(54) PALATINOSE FOR ENHANCING DIETARY SUPPLEMENT AND PHARMACEUTICAL DELIVERY

(76) Inventor: Bruce W. Kneller, Randolph, MA (US)

( * ) Notice: Subject to any disclaimer, the term of this patent is extended or adjusted under 35 U.S.C. 154(b) by 101 days.

This patent is subject to a terminal disclaimer.

(21) Appl. No.: 11/385,137

(22) Filed: Mar. 20, 2006

(65) Prior Publication Data

US 2006/0153899 A1 Jul. 13, 2006

Related U.S. Application Data

(60) Provisional application No. 60/663,384, filed on Mar. 19, 2005.

(51) Int. Cl.
*A01N 43/04* (2006.01)
*A61K 31/70* (2006.01)
*A61K 47/00* (2006.01)

(52) U.S. Cl. ......................................... 514/25; 424/439
(58) Field of Classification Search .................... 514/25; 424/439

See application file for complete search history.

(56) References Cited

U.S. PATENT DOCUMENTS

| 5,378,131 | A | | 1/1995 | Greenberg |
| 5,614,224 | A | * | 3/1997 | Womack ........................ 424/646 |
| 5,659,028 | A | | 8/1997 | Coussement et al. |
| 5,968,544 | A | * | 10/1999 | Howard et al. ................ 424/439 |
| 6,652,901 | B2 | | 11/2003 | Ishii |
| 6,713,116 | B1 | | 3/2004 | Aldrich et al. |
| 6,750,331 | B1 | | 6/2004 | Takaichi et al. |
| 2003/0143311 | A1 | | 7/2003 | Gillota |
| 2005/0002988 | A1 | * | 1/2005 | Mizumoto et al. ............ 424/439 |
| 2009/0181922 | A1 | | 7/2009 | Kneller |
| 2009/0281055 | A1 | | 11/2009 | Kneller |

FOREIGN PATENT DOCUMENTS

WO WO 03/022288 A1 * 6/2002

OTHER PUBLICATIONS

Mingrone, G. Greco, A.V., Capristo, E., Benedetti, G., Giancaterini, A., De Gaetano, A., Gasbarrini, G. (1999) L-Carnitine Improves Glucose Disposal in Type 2 Diabetic Patients. Journal of the American College of Nutrition, vol. 18, No. 1, p. 77-82.*
Hodgson, J.M., Watts, G.F., Playford, D.A., Burke, V., Croft, K.D. (2002) coenzyme Q10 improves blood pressure and glycaemic control: a controlled trial in subjects with type 2 diabetes. European Journal of clinical Nutrition, vol. 56, p. 1137-1142.*
Op 't Eijnde, B., Urso, B., Richter, E.A., Greenhaff, P.L., Hespel, P. (2001) Effect of Oral Creatine Supplementation on Human Muscle GLUT 4 Protein Content After Immobilization. Diabetes, vol. 50, p. 18-23.*
Salazar-Martinez, E., Willett, W.C., Ascherio, A., Manson, J.E., Leitzmann, M.F., Stampfer, M.J., Hu, F.B. (2004) Coffee Consumption and Risk for Type 2 Diabetes Mellitus. Annals of Internal Medicine, vol. 140, p. 1-8.*

Krastanov, A., Yoshida, T. (2003) Production of palatinose using *Serratia plymuthica* cells immobilized in chitosan. Journal of Industrial Microbiology and Biotechnology, vol. 30, p. 593-598.*
Arenas, J., Ricoy, Jr., Encinas, A.R., Pola, P., D'Iddio, S., Zeviani, M., Didonato, S., Corsi, M. (1991). Carnitine in Muscle, Serum, and Urine of Nonprofessional Athletes: Effects of Physical Exercise, Training, and L-Carnitine Administration. Muscle & Nerve, p. 598-604.*
Gaby, A.R. (1996) The Role of Coenzyme Q10 in Clinical Medicine: Part I. Alternative Medicine Review, vol. 1, No. 1, p. 11-16.*
Magkos, F., Kavouras, S.A. (2004) Caffeine and Ephedrine: Physiological, Metabolic and Performance-Enhancing Effects. Sports Medicine, vol. 34, No. 13, p. 871-889.*
Meissner, C., (2006) New Energy Profiles for Sports Drinks. Sachon-Fachzeitschriftenarchiv, fzarchiv.sachon.de BBII:56-57, Retrieved on-line Dec. 20, 2010.
Arai, H., Mizuno, A., Sakuma, M., Fukaya, M., Matsuo, K., Muto, K., Sasaki, H., Matsuura, M., Okumura, H., Yamamoto, H., Taketani, Y., Doi, T., Takeda, E. (2007) Effects of a palatinose-based liquid diet (Inslow) on glycemic control and the second-meal effect in healthy men. Metabolism Clinical and Experimental 56:115-121.
Oizumi, T., Daimon, M., Jimbu, Y., Kameda, W., Arawaka, N., Yamaguchi, H., Ohnuma, H., Sasaki, H., Kato, T. (2007) A Palatinose-Based Balanced Formula Improves Glucose Tolerance, Serum Free Fatty Acid Levels and Body Fat Composition. Tohoku J Exp Med 212:91-99. Salazar-Martinez, E., Willett, W.C., Ascherio, A., Manson, J.E., Leitzmann, M.F., Stampfer, M.J., Hu, F.B. (2004) Coffee Consumption and Risk for Type 2 Diabetes Mellitus. Ann. Intern Med. 140:1-8.
Fernie, A.R., Roessner, U., Geigenberger, P. (2001) The Sucrose Analog Palatinose Leads to a Stimulation of Sucrose Degradation and Starch Synthesis When Supplied to Discs of Growing Potato Tubers. Plant Physiology, 125:1967-1977.
Gerstner, G., (2003) How to Fortify Beverages with Calcium. Food Marketing & Technology, 16-19.

* cited by examiner

*Primary Examiner* — Scarlett Goon
(74) *Attorney, Agent, or Firm* — Morse, Barnes-Brown & Pendleton, P.C.; Lisa M. Treannie, Esq.

(57) ABSTRACT

The present invention is directed to a dietary supplement comprising palatinose or a derivative thereof. The dietary supplement may be a nutritional product, a sports performance product, a weight loss product or a meal replacement product. The present invention is also directed to a method of increasing the absorption of a compound into the bloodstream, cells and tissue comprising administering palatinose, or a derivative thereof, in combination with the compound. The present invention also relates to a diluent for parenteral compounds. The diluent comprises palatinose or a derivative thereof. Another aspect of the present invention is directed to a method of decreasing the recovery time to pre-performance levels of total adenosine triphosphate (ATP) levels in a mammal comprising administering palatinose, or a derivative thereof, to the mammal. The present invention is further directed to a method of supplying a compound to a diabetic patient, burn victim patient or trauma victim patient. The method comprises administering palatinose, or a derivative thereof, in combination with the compound.

12 Claims, No Drawings

PALATINOSE FOR ENHANCING DIETARY SUPPLEMENT AND PHARMACEUTICAL DELIVERY

This application claims the benefit of U.S. Provisional Application No. 60/663,384, filed Mar. 19, 2005, which is incorporated herein by reference.

BACKGROUND OF THE INVENTION

1. Technical Field

The present invention relates to a disaccharide for therapeutic use. More particularly, the invention relates to the use of palatinose (6-O-alpha-D-glucopyranosyl-D-fructofuranose) to increase the efficacy of dietary supplements and pharmaceuticals.

2. Description of Related Art

Palatinose is a disaccharide consisting of d-glucose and d-fructose connected by an alpha-1,6-glycosidic linkage. It is also referred to as 6-O-alpha-D-glucopyranosyl-D-fructofuranose and as isomaltulose, and is readily produced commercially from sucrose by enzymatic rearrangement. Palatinose has a taste and appearance similar to that of sucrose. Because of the rate by which it is metabolized, it presents potential dietary and therapeutic uses.

Most sugars are rapidly absorbed after consumption. Therein, after oral administration of a significant amount of sucrose (common table sugar), blood glucose levels rise quickly. This is followed by a quick rise in insulin levels which brings the blood glucose level back down. The digestion and absorption of palatinose is unlike other sugars. It is completely digested and absorbed at a much slower speed, equivalent to about ⅕ of that for sucrose. Thus, after oral administration of palatinose, blood glucose and insulin levels rise more slowly and reach a lower maxima compared to sucrose. Because of this characteristic, palatinose is well suited as a sucrose replacement for diabetics and others with prediabetic dispositions.

Another benefit of palatinose is its non-cariogenic quality, i.e., does not promote tooth decay. It is used as a substitute for other sugars, particularly in the candy and chewing gum industry. Moreover, it is an improvement over other sugar-substitutes because it does not cause abdominal discomfort or diarrhea, a side-effect of many sugar alcohols.

Many compounds, including nutrients and dietary supplements, depend on the presence of a sugar for absorption from the gastrointestinal tract as well as for absorption from the plasma into various tissues/cells of the body. Studies have demonstrated that the performance enhancing supplement creatine is better absorbed into human skeletal muscle when taken with glucose. Certain amino acids are also more readily absorbed when administered with glucose. However, sucrose and other sugars are not ideal for use in combination with nutrient supplements. Sucrose is rapidly digested and absorbed into the blood stream. This results in a rapid rise in circulating insulin levels which quickly lowers circulating glucose levels. As a result, many compounds and nutrients administered in combination with sucrose may not be absorbed because of the short duration of the "sugar effect."

Moreover, excessive amounts of sugar can cause an increase in body fat, decreased sensitivity to insulin and tooth decay. Sugar substitutes, which are generally sugar alcohols, are also inadequate for purposes of aiding absorption. Although they are hydrolyzed and digested slowly, they often cause abdominal discomfort and diarrhea. Thus, an improved sugar is needed for use in the absorption of dietary supplement products as well as other therapeutic compounds.

SUMMARY OF THE INVENTION

The present invention solves the above-described problem by providing a dietary supplement comprising palatinose or a derivative thereof, a sugar, a stimulant, at least one amino acid or derivative thereof, and at least one mineral. The dietary supplement may be a nutritional product, a sports performance product, a weight loss product, or a meal replacement product. Palatinose enhances absorption of the dietary supplement components into the bloodstream, cells and tissue.

More particularly, the dietary supplement may comprise palatinose or a derivative thereof; amylose; glucose; a methylxanthine such as caffeine or theobromine or both; arginine or a salt, ester or chelate thereof; creatine or a salt, ester or chelate thereof; disodium adenosine triphosphate; calcium carbonate; sodium bicarbonate; and glucuronolactone. This dietary supplement formulation increases the athletic performance of a mammal during an approximately one to three hour period.

Still more particularly, the dietary supplement of the present invention may comprise palatinose or a derivative thereof; trehalose; amylose; amylopectin; L-carnosine; calcium carbonate; sodium bicarbonate; sulbutiamine or fursultiamine; disodium adenosine triphosphate; orotic acid; vinpocetine or rhodiola rosea; and cellulose or another undigestible bulk forming starch. This dietary supplement formulation increases the athletic performance of a mammal during an approximately three to eight hour period.

Another aspect of the present invention is directed to a method of increasing the absorption of a compound into the bloodstream, cells and tissue. The method includes administering palatinose or a derivative thereof in combination with the compound.

More particularly, the compound may be a dietary supplement, a nutrient, a pharmaceutical, or a vaccine. If the compound is a dietary supplement formulation, the method may comprise adding palatinose or a derivative thereof to the dietary supplement formulation prior to administration. If the compound is a pharmaceutical formulation, the method may comprise adding palatinose or a derivative thereof to the pharmaceutical formulation.

Still, another aspect of the present invention is directed to a diluent for parenteral compounds, wherein the diluent comprises palatinose or a derivative thereof. The parenteral compound may be a dietary supplement, a nutrient, a pharmaceutical, or a vaccine.

Yet, another aspect of the present invention is directed to a method of decreasing recovery time to pre-performance levels of total adenosine triphosphate (ATP) levels in a mammal comprising administering palatinose, or derivative thereof, to the mammal. The palatinose or derivative thereof may be administered orally or parenterally. Preferably, the palatinose or derivative thereof is administered in a dose between about 0.5 grams and about 200 grams.

The present invention is also directed to a method of supplying a compound to a diabetic patient, burn victim patient or trauma victim patient. The method includes administering palatinose, or a derivative thereof, in combination with the compound. The compound may be a nutrient, dietary supplement, or pharmaceutical. The compound and palatinose or derivative thereof, may be administered orally or parenterally.

In addition, the palatinose or derivative thereof is preferably administered in a dose between about 0.5 grams and about 200 grams.

Other features and advantages of the present invention will become apparent upon reading the following detailed description of embodiments of the invention, when taken in conjunction with the appended claims.

DETAILED DESCRIPTION

Studies have demonstrated that the presence of sugar directly enhances nutrient absorption into various tissues and cells. For example, a mixture of arginine and glucose is more efficiently absorbed into the vascular endothelium than arginine alone. Other studies have shown that nutrients and ergogenic sports performance products depend on the indirect presence of sugar for absorption wherein increased levels of insulin enhance the absorption of nutrients into the tissues and cells.

Palatinose offers an improvement over other sugars, including glucose, in that it is metabolized much slower by the gastrointestinal tract thereby extending the time that the "sugar effect," both direct and indirect, can have on the absorption of dietary supplements, nutrients, pharmaceuticals or vaccines. Rather than enter the blood stream, rapidly rise and fall, palatinose leads to gradual increases and sustained levels of glucose and insulin. This allows greater time and opportunity for the absorption of various compounds. With respect to dietary supplements, the end result may be greater energy, alertness, athletic performance and/or muscle development.

Moreover, replacing common sugars with palatinose presents other advantages. Preventing surges in blood glucose and insulin levels may help in the management and prevention of obesity, diabetes and cardiovascular disease. Recent studies have also provided evidence that palatinose may also have a positive effect on mental concentration. And unlike other sugars, palatinose does not promote tooth decay.

The Dietary Supplement Health and Education Act of 1994, commonly referred to as DSHEA, defines "dietary supplement" as any product (except tobacco) that contains at least one of the following: (1) a vitamin, (2) a mineral, (3) an herb or botanical, (4) an amino acid, (5) a dietary substance "for use to supplement the diet by increasing total dietary intake," or (6) any concentrate, metabolite, constituent, extract, or combination of any of the aforementioned ingredients. Examples of dietary supplements include, but are not limited to nutritional products; sports performance products, including ergogenic sports performing products; weight loss products; and meal replacement products. Dietary supplements may exist in various forms, including, but not limited to tablets, capsules, caplets, powders, drinks including shakes, solid food items including snack bars, etc.

In one embodiment, the dietary supplement of the present invention includes palatinose or a derivative thereof, a sugar, a stimulant, at least one amino acid or derivative thereof, and at least one mineral. For example, a dietary supplement designed to increase the athletic performance of a mammal during a one to three hour sports activity period, preferably comprises palatinose or a derivative thereof; amylose; glucose; a methylxanthine such as caffeine or theobromine or both; arginine or a salt, ester or chelate thereof; creatine or a salt, ester or chelate thereof; disodium adenosine triphosphate; calcium carbonate; sodium bicarbonate; and glucuronolactone.

Alternatively, the dietary supplement of the present invention may comprise palatinose or a derivative thereof; trehalose; amylose; amylopectin; L-carnosine; calcium carbonate; sodium bicarbonate; sulbutiamine or fursultiamine; disodium adenosine phosphate; orotic acid; vinpocetine or rhodiola rosea; cellulose or another undigestible bulk forming starch; and perhaps at least one B vitamin. This dietary supplement formulation increases the athletic performance of a mammal during an approximately three to eight hour period.

Other preferred dietary supplement formulations of the present invention may comprise palatinose or a derivative thereof, and any or all of the following: water; carbon dioxide; creatine or a salt, ester or chelate thereof; carnitine or a salt, ester or chelate thereof; taurine or a salt, ester or chelate thereof; arginine or a salt, ester or chelate thereof; citrulline or a salt, ester or chelate thereof; carnosine or a salt, ester or chelate thereof; pyruvate or a salt, ester or chelate thereof; ribose; amylase; amylopectin; tyrosine or a salt, ester or chelate thereof; tyramine or a salt, ester or chelate thereof; histidine or a salt, ester or chelate thereof; alanine or a salt, ester or chelate thereof; phenylalanine or a salt, ester or chelate thereof; adenosine mono, di or triphosphate, or a salt, ester or chelate thereof; alpha lipoic acid, or a salt, ester or chelate thereof; 4-hydroxy-isoleucine; d-pinitol; ornithine or a salt, ester or chelate thereof; sodium or any salt thereof; potassium or any salt thereof; zinc or any salt thereof; magnesium or any salt thereof; iron or any salt thereof; chromium or any salt thereof; calcium or any salt thereof; vitamin B-1; vitamin B-2; vitamin B-3; vitamin B-6; vitamin B-12; pantothenic acid; folic acid; vitamin C; 7-keto-DHEA, or any ester or ether thereof; 7-hydroxy-DHEA or any ester thereof; caffeine; octopamine; norsynephrine; synephrine; ephedrine; hordenine; theobromine; evodiamine; phenylephrine; insulin; metformin; corosolic acid; glucuronolactone; ginger; ginseng; ginko biloba; rhodiola rosea; fenugreek; epicatechin; epicatechin-3-gallate; epigallocatechin; epigallocatecin-3-gallate; glutamine; branched chain amino acids or any salts or esters thereof; any chelate of any amino acid; 6-methyluracil; phosphocreatinine; orotic acid; 5-hydroxytryptophan; vinpocetine; sucralose; fructose; galactose; maltodextrin; glucose; DMAE; DMG; TMG; coenzyme Q-10, sulbutiamine; fursultiamine; octotiamine; adrafanil; choline; phosphatidylcholine; and phosphatidylserine.

Due to the presence of palatinose, or derivative thereof, in the dietary supplements of the present invention, these dietary supplements increase athletic performance, energy, strength, percent fat-free muscle mass, muscle development, mental concentration and alertness, and stamina in mammals.

It should be understood that palatinose may be added to any dietary supplement formulation to enhance the effects of and improve the absorption of the dietary supplement, and the present invention is intended to encompass such improved formulations. It should also be understood that use of the palatinose in any of the embodiments or methods of the present invention may be substituted by any derivative of palatinose.

Preferably, the concentration of palatinose, or derivative thereof, in the dietary supplement is between approximately 1% and approximately 85%. More preferably, the concentration of palatinose in the dietary supplement is between approximately 10% and approximately 50%. Furthermore, the palatinose present in the dietary supplement is desirably administered in a dose between about 0.5 grams and about 200 grams.

The present invention is also related to a method of increasing the absorption of a compound into the bloodstream, cells and tissue by administering palatinose, or a derivative thereof, in combination with the compound. Palatinose may be used to increase the absorption of any compound in the method of the present invention, including compounds used to treat any disease or illness. Exemplary compounds for use in the present invention include, but are not limited to a dietary supplement, a nutrient, a pharmaceutical, or a vaccine. When palatinose is used to increase the absorption of particular compounds, including dietary supplements and nutrients, the fatigue associated with an athletic performance of a mammal is reduced.

In addition, because palatinose maintains a more constant elevation of blood sugar levels as opposed to other sugars, an optimal maximum rate of adenosine triphosphate (ATP) synthesis in cells can be maintained for several hours. Most sugars, including glucose, peak in the plasma about 45 to 60 minutes post absorption and then an insulin spike drives this level down rapidly, leading to pre-prandial (or lower) levels of plasma sugar. When the plasma sugar levels decrease, ATP synthesis also decreases. Palatinose maintains a slightly heightened plasma sugar level for a longer period of time. As a result, mitochondria have access to optimal levels of carbohydrates for approximately 6 to 8 hours, thereby allowing for heightened and continued ATP synthesis. Accordingly, the administration of palatinose, or a derivative thereof, to a mammal decreases the recovery time to pre-activity performance levels of total ATP in the mammal. Preferably, palatinose is administered prior to the sports performance.

The method of the present invention may include adding palatinose, or a derivative thereof, to a dietary supplement formulation, pharmaceutical formulation or vaccine formulation prior to administering the respective compounds. Preferably, the concentration of palatinose or derivative thereof, in the dietary supplement, pharmaceutical, vaccine or other formulation, is between approximately 1% and approximately 85%. More preferably, the concentration of palatinose or derivative thereof, in the dietary supplement, pharmaceutical, vaccine or other formulation, is between approximately 10% and approximately 50%. Furthermore, the palatinose, or derivative thereof, is desirably administered in a dose between about 0.5 grams and about 200 grams.

Additional examples of compounds that may be used in the method of the present invention include, but are not limited to phosphatidyserine; S-adenosyl-methionine; nicotinamide adenine dinucleotide; any cephalosporin antibiotic; any macrolide antibiotic; any aminoglycoside; antibiotic; any penicillin antibiotic; any fluroquinolone antibiotic; any tetracycline antibiotic; chloramphenicol; any protease inhibitor antiviral; any nucleoside analog antiviral; any reverse transcriptase inhibitor antiviral; any polyene or membrane active antimycotic; any azole or inhibitor of ergosterol biosynthesis antimycotics; griseofulvin; flucytosine; capsofungin; mycafungin; any pneuraminidase inhibitor antiviral; any polymerase inhibitor antiviral; any class of interferon; any class of interleukin; any type of human growth hormone; any type of insulin growth factor or insulin like growth factor; any type of anti-vascular endothelial growth factor antibodies; any alkylating agent including those used to treat cancer of any type; any antimetabolite agent including those used to treat cancer of any type; any plant alkaloid agent including those used to treat cancer of any type; doxorubicin or any salt, ester, or chelate thereof; mitoxantrone or any salt, ester or chelate thereof; bleomycin or any salt, ester, ether or chelate thereof; platinum or any salt, ester, ether or chelate thereof; paclitaxel; docetaxel; epoeitin alfa; and darboepoeitin alfa.

The compound and palatinose may be administered by any method known to those having skill in the art including, but not limited to oral and parenteral administration. The compound and palatinose may also be administered in a solution of water or saline, wherein the saline is hypotonic, hypertonic or normotonic saline. Palatinose, or a derivative thereof, may also be used as a diluent for any parenteral compound, including, but not limited to dietary supplements, nutrients, pharmaceuticals and vaccines.

Palatinose is particularly useful for supplying any compound, including nutrients and pharmaceuticals, to patients, such as diabetic, burn victim, and trauma victim patients.

It should be understood that the foregoing relates to exemplary embodiments of the invention and that modifications may be made without departing from the spirit and scope of the invention as set forth in the following claims.

What is claimed is:

1. A dietary supplement comprising isomaltulose and one or more compounds selected from the group consisting of creatine and a creatine salt, wherein the concentration of isomaltulose is between about 10% and about 85%.

2. The dietary supplement of claim 1, wherein the dietary supplement is a nutritional product, a sports performance product, a weight loss product, or a meal replacement product.

3. The dietary supplement of claim 1, wherein the concentration of isomaltulose is between about 10% and about 50%.

4. The dietary supplement of claim 1, wherein the dietary supplement further comprises one or more compounds selected from the group consisting of a sugar, a stimulant, an amino acid, and a mineral.

5. The dietary supplement of claim 1, wherein the dietary supplement further comprises one or more compounds selected from the group consisting of: trehalose; amylose; glucose; a methylxanthine; arginine or a salt, ester or chelate thereof; amylopectin; L-carnosine; calcium carbonate; sodium bicarbonate; glucuronolactone; sulbutiamine or fursultiamine; disodium adenosine phosphate; adenosine triphosphate; orotic acid; vinpocetine or rhodiola rosea; cellulose; and starch.

6. The dietary supplement of claim 4, further comprising one or more of the following selected from the group consisting of carnitine or a salt, ester or chelate thereof; taurine or a salt, ester or chelate thereof; arginine or a salt, ester or chelate thereof; citrulline or a salt, ester or chelate thereof; carnosine or a salt, ester or chelate thereof; pyruvate or a salt, ester or chelate thereof; tyrosine or a salt, ester or chelate thereof; tyramine or a salt, ester or chelate thereof; histidine or a salt, ester or chelate thereof; alanine or a salt, ester or chelate thereof; phenylalanine or a salt, ester or chelate thereof; 4-hydroxy-isoleucine; ornithine or a salt, ester or chelate thereof; glutamine; branched chain amino acids or a salt, ester or chelate thereof; an amino acid chelate; 5-hydroxy-tryptophan; and choline.

7. The dietary supplement of claim 1 further comprising Coenzyme Q-10 and one or more of carnitine, a carnitine salt, a carnitine ester and a carnitine chelate.

8. The dietary supplement of claim 1 further comprising one or more of carnitine, a carnitine salt, a carnitine ester and a carnitine chelate.

9. The dietary supplement of claim 1 further comprising coenzyme Q10.

10. The dietary supplement of claim 1 further comprising one or more stimulants.

11. The dietary supplement of claim 10 wherein the one or more stimulants are selected from the group consisting of caffeine; octopamine; norsynephrine; synephrine; ephedrine; hordenine; theobromine; sulbutiamine; fursultiamine; octotiamine; and adrafanil.

12. The dietary supplement of any one of claim 1, 2, 4, 5, 3, 7 or 6-9, further comprising carbon dioxide.

* * * * *

UNITED STATES PATENT AND TRADEMARK OFFICE
CERTIFICATE OF CORRECTION

Page 1 of 1

PATENT NO. : 8,283,327 B2
APPLICATION NO. : 11/385137
DATED : October 9, 2012
INVENTOR(S) : Kneller It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 164 days.

Signed and Sealed this
Second Day of September, 2014

Michelle K. Lee
*Deputy Director of the United States Patent and Trademark Office*